United States Patent [19]

Fukami et al.

[11] Patent Number: 4,599,360
[45] Date of Patent: Jul. 8, 1986

[54] OPHTHALMIC ANTI-INFLAMMATORY AGENTS

[75] Inventors: Masaharu Fukami; Atsusuke Terada; Kazue Hasegawa, all of Hiromachi, Japan

[73] Assignee: Sankyo Company Limited, Tokyo, Japan

[21] Appl. No.: 639,376

[22] Filed: Aug. 9, 1984

[30] Foreign Application Priority Data

Aug. 10, 1983 [JP] Japan .................. 58-146147

[51] Int. Cl.$^4$ .............................. A61K 31/19
[52] U.S. Cl. .................... 514/570; 514/914
[58] Field of Search ............... 514/570, 914

[56] References Cited

U.S. PATENT DOCUMENTS

| | | |
|---|---|---|
| 3,228,831 | 1/1966 | Nicholson et al. ............ 514/570 |
| 3,865,949 | 2/1975 | Greig ............................ 514/570 |
| 4,161,538 | 7/1979 | Terada et al. ................. 514/570 |
| 4,254,274 | 3/1981 | Terada et al. . |
| 4,400,534 | 8/1983 | Terada et al. . |
| 4,461,912 | 7/1984 | Terada et al. . |

FOREIGN PATENT DOCUMENTS 2078732 2/1984 United Kingdom .

OTHER PUBLICATIONS

Chem. Abst. 94:103,020(b) (1981)–Sankyo Co., Ltd.
Chem. Abst. 96:199326w (1982)–Atsusuke et al.
Chem. Abst. 96:45982v (1982)–Misaka et al.
Chem. Abst. 97:215760m (1982)–Terada et al.
Chem. Abst. 98:100904q (1983)–Matsuda et al.
Chem. Abst. 99:262f (1983)–Yamaguchi et al.
Chem. Abst. 100:51183c (1984)–Terada et al.
Chem. Abst. 102:95400s (1985)–Terada et al.

*Primary Examiner*—Douglas W. Robinson
*Attorney, Agent, or Firm*—Frishauf, Holtz, Goodman & Woodward

[57] ABSTRACT

Compounds of formula:

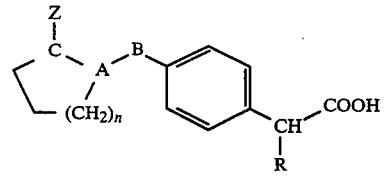

(wherein R represents hydrogen or methyl, $>$A—B— represents a $>$CH—CH$_2$— or $>$C=CH— group; $>$C—Z represents a $>$C=O or $>$CH—OH group; and n represents 1 or 2) and ophthalmically acceptable salts and esters thereof are useful as ophthalmic anti-inflammatory agents.

19 Claims, No Drawings

OPHTHALMIC ANTI-INFLAMMATORY AGENTS

BACKGROUND TO THE INVENTION

The present invention relates to a method for the treatment or prophylaxis of ocular inflammation by the administration of an anti-inflammatory agent and also provides compositions containing this agent and especially formulated for ophthalmic use.

The ophthalmic agent of the present invention is a member of the class of phenylacetic acid derivatives and the compounds employed as such agents have been disclosed in, for example, United Kingdom Pat. Specification No. 1,580,113 and the corresponding U.S. Pat. No. 4,161,538, United Kingdom Pat. Specification No. 2,002,762 and the corresponding U.S. Pat. No. 4,254,274, United Kingdom Pat. No. Specification No. 2,078,732 and the corresponding U.S. Pat. No. 4,400,534, European Pat. Publication No. 55,588, United Kingdom Pat. Specification No. 2,113,214 and the corresponding U.S. Pat. No. 4,461,912 and U.S. patent application Ser. No. 600,372, filed Apr. 16, 1984. Of these, United Kingdom Pat. Specification No. 2,078,732 describes the use of these phenylacetic acid derivatives for topical administration, whilst the remaining documents referred to disclose the use of the compounds for internal (i.e. oral or parenteral) use.

We have now discovered that these compounds can be used to prevent or inhibit inflammation of the eye. This is particularly surprising since anti-inflammatory compounds are not commonly capable of being used in such a variety of ways. For example, aspirin and many other analgesic anti-inflammatory agents may be administered systemically, usually by the oral route, but are not used for topical administration. On the other hand, methyl salicylate, which is used externally for rheumatic conditions, is considered too toxic for internal administration, and similarly compounds such as bendazac and bufexamac are normally only used externally. Moreover, phenylbutazone, ibuprofen and indomethacin, which are all well-known and commonly used anti-inflammatory agents, and which are cited in the above documents for comparative purposes, are all known to have adverse effects upon the eye. For example, phenylbutazone has been reported to cause conjunctivitis, toxic amblyopia, Stevens-Johnson syndrome, adhesion of lids to eyeballs, gross scarring of lids, corneal ulceration and scarring, vascularisation of the cornea, loss of vision and possible retinal haemorrhage [H. I. Silverman, Am. J. Optom., 49, 335 (1972)]. Indomethacin has been reported to cause mydriasis, diplopia and toxic amblyopia (H. I. Silveman, op. cit.), decreased retinal sensitivity and corneal deposits [C. A. Burns, Am. J. Ophthal., 66, 825 (1968)] and a variety of other corneal and retinal effects. Ibuprofen has been reported to cause a variety of visual defects, including toxic amblyopia [L. M. T. Collum and D. I. Bowen, Br. J. Ophthal., 55, 472 (1971)]. Accordingly, use of these compounds for treatment of eye disorders is hardly likely to be considered. There is, therefore, normally a clear distinction between anti-inflammatory agents employed for systemic, topical and ophthalmic use.

We have now surprisingly discovered that the aforementioned phenylacetic acid derivatives can be employed for the treatment of ocular disorders.

BRIEF SUMMARY OF INVENTION

The present invention relates to a method for the treatment or prophylaxis of ocular inflammation by the administration to the mammalian eye, which may be human, of an anti-inflammatory agent, wherein the anti-inflammatory agent comprises at least one phenylacetic acid derivative of formula:

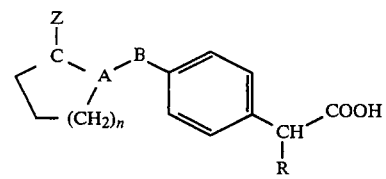

[wherein:
R represents the hydrogen atom or the methyl group;
>A—B— represents a >CH—CH$_2$— or >C=CH— group;
>C—Z represents a >C=O (carbonyl) group or a >CH—OH group; and
n is 1 or 2]
or an ophthalmically acceptable salt or ester thereof.

The invention also provides a pharmaceutical composition formulated for ophthalmic use and including, as the active ingredient, at least one of the phenylacetic acid derivatives defined above.

DETAILED DESCRIPTION OF INVENTION

Phenylacetic acid derivatives which may be employed in the method and composition of the present invention are disclosed in United Kingdom Pat. Specification No. 1,580,113, United Kingdom Pat. Specification No. 2,002,762, United Kingdom Pat. Specification No. 2,078,723, European Pat. Publication No. 55,588 and United Kingdom Pat. Specification No. 2,113,214, all of which were published before the priority date hereof and which are incorporated herein by reference. Examples of these compounds and descriptions of how they may be prepared are given in these United Kingdom Patent Specifications and European Patent Publication.

The aforementioned U.S. patent application Ser. No. 600,372 discloses compounds of formula (I):

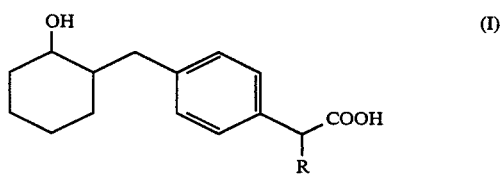

(wherein R represents hydrogen or a C$_1$–C$_3$ alkyl group) and pharmaceutically acceptable salts and esters thereof.

They may be prepared by:

(a) reducing a compound of formula (IVa):

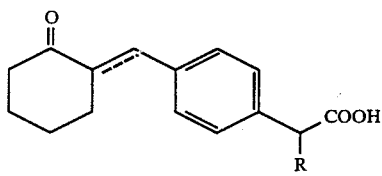

(in which R is as defined above an ⟶ represents a single or double carbon-carbon bond) to give the compound of formula (I):

(b) optionally salifying or esterifying the compound of formula (I); and (c) optionally separating the product of step (a) or (b) [the compound of formula (I) or its salt or ester] into the cis and trans isomers.

Examples of the compounds are:
(±)-2-[4-(cis-2-hydroxycyclohexylmethyl)phenyl]propionic acid;
(±)-2-[4-(trans-2-hydroxycyclohexylmethyl)phenyl]propionic acid.

Preferred compounds for use in the present invention are as follows:
2-[4-(2-oxocyclopentylmethyl)phenyl]propionic acid;
2-[4-(2-oxocyclopentylmethyl)phenyl]acetic acid;
2-[4-(2-oxocyclohexylmethyl)phenyl]propionic acid;
2-[4-(2-oxocyclopentylidenemethyl)phenyl]propionic acid;
2-[4-(2-oxocyclohexylidenemethyl)phenyl]propionic acid;
2-[4-(2-hydroxycyclopentylidenemethyl)phenyl]propionic acid;
2-[4-(2-hydroxycyclohexylidenemethyl)phenyl]propionic acid;
2-[4-(trans-2-hydroxycyclopentylmethyl)phenyl]propionic acid;
2-[4-(trans-2-hydroxycyclohexylmethyl)phenyl]propionic acid;
2-[4-(cis-2-hydroxycyclopentylmethyl)phenyl]propionic acid; and
2-[4-(cis-2-hydroxycyclohexylmethyl)phenyl]propionic acid.

As can clearly be seen from the above list of preferred compounds, the compounds employed in the invention can exist in the form of geometric isomers and the present invention contemplates the use of the individual isolated isomers, as well as mixtures thereof.

The compounds of the invention may also exist in the form of salts of the compounds represented by the above formula. The nature of the salts is not critical to the invention although, of course, since they are intended for administration to the eye, the salts should be ophthalmically acceptable salts. Examples of such salts include the alkali and alkaline earth metal salts (such as the sodium or calcium salts), the aluminium salt, salts with organic amines (such as triethylamine, dicyclohexylamine, dibenzylamine, morpholine, piperidine or N-ethylpiperidine) and salts with basic amino acids (such as lysine or arginine). The salts may be prepared from the free carboxylic acids of the above formula by conventional salification processes.

The compounds of the present invention also include the esters of compounds of the above formula. Examples of such esters include $C_1$–$C_6$ alkyl esters, aralkyl esters and pyridylmethyl esters. Examples of alkyl esters include the methyl, ethyl, propyl, isopropyl, butyl, isobutyl, pentyl, isopentyl, hexyl and isohexyl esters; of these, $C_1$–$C_4$ alkyl esters are preferred, particularly the ethyl, methyl, propyl, isopropyl and butyl esters. Examples of aralkyl esters include the benzyl and phenethyl esters, in which the aromatic ring may be substituted or unsubstituted. Where it is substituted, the substituents may be one or more of the following: $C_1$–$C_6$ groups, e.g. methyl, ethyl, propyl or isopropyl groups; $C_1$–$C_6$ alkoxy groups, e.g. methoxy, ethoxy, propoxy or isopropoxy groups; halogen atoms, e.g. fluorine, chlorine or bromine atoms; or trifluoromethyl groups. In the case of pyridylmethyl esters, these may be the 2-, 3- or 4-pyridylmethyl esters.

Of the salts and esters referred to above, the sodium salt is particularly preferred and, most particularly, we prefer the sodium salts of the preferred compounds of the invention listed above.

In recent years, various research has been carried out to reveal a relationship between ophthalmic inflammations and prostaglandins. For example, it is believed that prostaglandins migrating from the ocular tissues during operation on the anterior portion of the eye increase the permeability of the blood-aqueous barrier, thus giving rise to atropine antagonistic moisis, post-operative inflammation, increases in intra-ocular tension and various other undesirable effects [J. D. Miller, K. E. Eakins and M. Atwal, Invest. Ophthalmol., 12, 939 (1973) and P. Bhattacherjee, Brit. J. Pharmacol., 54, 489 (1975)]. Accordingly, it has been hypothesized that inflammation could be suppressed and the other symptoms referred to could be remitted if the biosynthesis of prostaglandins, which is regarded as the cause of these effects, could be inhibited.

However, where a non-steroidal anti-inflammatory agent capable of inhibiting the biosynthesis of prostaglandins is administered orally, the proportion of the administered dose which actually has any effect on the eye is very small and it is, therefore, necessary to increase the dose, thus increasing side-effects, such as disorders of the digestive tract. Accordingly, in ophthalmic therapy, it is desirable to develop drugs which can be administered locally and have a local effect.

We have surprisingly found that the compounds of the invention fulfil these requirements.

In view of the sensitivity of the tissues of the eye, formulations for ophthalmic use differ substantially from formulations for other applications, in constituents, concentrations, methods of presentation, sterility or many other ways, as is well-recognized in the art. For example, the compounds of the invention may be formulated as eye drops (which are sterile aqueous or oily solutions or suspensions for instillation into the eye and which are usually prepared in a vehicle which is bactericidal and fungicidal), as eye lotions (which are sterile aqueous solutions which are commonly used undiluted in first-aid or domiciliary treatment; during preparation, considerable care is taken to destroy and exclude microorganisms) or eye ointments (which are sterile preparations for application to the conjunctival sac or lid margin; again, they must be prepared under highly aseptic conditions). The concentration of the compound of the invention in the formulation will, of course, vary depending upon the nature of the preparation; normally, a concentration of from 0.05 to 5% by weight, more preferably from 0.1 to 2% by weight of the formulation is employed. The composition of the invention is preferably administered to the eye several times per day.

The invention is further illustrated by the following Examples, of which Examples 1 to 6 illustrate the preparation of various formulations according to the present invention, whilst Examples 7–9 illustrate the biological activity of the compounds.

In the Examples, the compounds used are identified by the following codes:
A: sodium 2-[4-(2-oxocyclopentylmethyl)phenyl]propionate;
B: sodium 2-[4-(2-oxocyclohexylidenemethyl)phenyl]propionate;
C: sodium 2-[4-(trans-2-hydroxycyclopentylmethyl)phenyl]propionate;
D: 2-[4-(2-oxocyclohexylidenemethyl)phenyl]propionic acid—the free acid form of Compound B.

EXAMPLE 1

Eye Lotion

The following ingredients were mixed under sterile conditions to prepare an eye lotion containing Compound A at a concentration of 1% by weight:

| Compound A | 10 mg |
| --- | --- |
| Disodium hydrogen phosphate | 2 mg |
| Sodium chloride | 5 mg |
| Benzalkonium chloride | 0.1 mg |
| 1N Aqueous sodium hydroxide | q.s. |
| Water to total | 1 ml |
| | (pH 7.5) |

EXAMPLE 2

Eye Lotion

An eye lotion identical with that produced in Example 1 was prepared but replacing Compound A by Compound B.

EXAMPLE 3

Eye Lotion

An eye lotion containing 0.1% by weight of Compound A was prepared from:

| Compound A | 1.0 mg |
| --- | --- |
| Disodium hydrogen phosphate | 2.0 mg |
| Sodium chloride | 7.0 mg |
| Benzalkonium chloride | 0.1 mg |
| 1N Aqueous sodium hydroxide | q.s. |
| Water to total | 1 ml |
| | (pH 7.5) |

EXAMPLE 4

Eye Ointment

An eye ointment containing 1% by weight of Compound A was prepared from (parts are by weight):

| Compound A | 1.0 part |
| --- | --- |
| Plastibase-50W | 99.0 parts |
| Total | 100.0 parts |

Plastibase-50W is a trade name for an ointment base available from E. R. Squibb and Sons Inc., U.S.A., and is composed of polyethylene and liquid paraffin.

EXAMPLE 5

Eye Drops

Eye drops were prepared by mixing the following under sterile conditions (parts are by weight):

| Compound B | 1.0 part |
| --- | --- |
| Sodium chloride | 0.45 part |
| Benzethonium chloride | 0.01 part |
| Boric acid | 0.40 part |
| 1N Aqueous sodium hydroxide | q.s. |
| Distilled water to total | 100 parts |

EXAMPLE 6

Eye Ointment

An eye ointment was prepared by mixing the following ingredients (parts are by weight):

| Compound B | 1.0 part |
| --- | --- |
| Distilled water | 5.0 parts |
| Lanolin | 10.0 parts |
| White petroleum | 84.0 parts |
| Total | 100.0 parts |

EXAMPLE 7

Inhibitory Effect on the Increase in Protein in the Secondary Aqueous Humour In this experiment, the eye lotion employed was that prepared as described in Example 1, 2, or 3. The test animals were male albino Japanese rabbits of body weight about 3.0 kg. The animals were employed in groups of four for each lotion under test and the results are given as averages over the four test animals.

Each test lotion was instilled 4 times, at intervals of 30 minutes, each time in an amount of 0.5 ml into one of the eyes of the test animal. At the same time, physiological saline was instilled in the same amount into the other eye, as a control.

30 minutes after the first instillation, the anterior chambers of both eyes were tapped by means of a 27G injector needle through the cornea, under anaesthetic, with an ophthalmic solution containing 0.4% by weight of Benoxil (registered trade mark) to collect around 0.2 ml of an aqueous humour from the anterior chambers of the eye (the primary aqueous humour).

2 hours after collection of this primary aqueous humour, a secondary aqueous humour was collected in the same manner in an amount of about 0.2 ml.

The concentrations of protein in both aqueous humours were determined quantitatively by the Lowry method [O. H. Lowry et al., J. Biol. Chem. 193,265 (1951)]. From this was calculated the increase in protein concentration (mg/ml) for each rabbit, i.e. the protein concentrated in the second aqueous humour less the protein concentration in the first aqueous humour. The results were averaged over the four animals in each group and are reported in Table 1 as the average value plus or minus the statistical error. Also calculated from these values and from the appropriate control values was the percentage inhibition.

TABLE 1

| Lotion of Example | Protein increase (mg/ml) | Percent Inhibition |
|---|---|---|
| 1 | 5.0 ± 1.2 | 84.8 ± 2.9 |
| Control | 32.6 ± 5.7 | |
| 2 | 11.7 ± 5.8 | 81.2 ± 8.1 |
| Control | 57.2 ± 5.2 | |
| 3 | 14.0 ± 1.2 | 58.7 ± 8.8 |
| Control | 36.6 ± 5.3 | |

As can be seen from the above Table, the concentrations of protein in the secondary aqueous humour are significantly lower in eyes treated with either compound of the invention than in the control eyes. In those cases where the eyes were treated with a lotion containing 1% by weight of the compound of the invention, the percentage inhibition of protein increase was in excess of 80%; even where the lotion contained only 0.1% by weight of the compound of the invention, the percentage inhibition was about 59%. These results suggest that destruction of the blood-aqueous barrier by tapping of the anterior chambers of the eyes was apparently inhibited.

EXAMPLE 8

Eye Irritation Test

The irritation to the eyes caused by relatively highly concentrated solutions of the compounds of the invention was determined by the Draize method [J. H. Draize et al. J. Pharmacol. Exp. Ther., 82, 377 (1944)] and evaluated by the method of Kay and Calandra [J. H. Kay and J. C. Calandra, J. Soc. Cosmet. Chem., 13, 281 (1962)].

The test solution employed in the present experiment was a simple solution of 10% or 20% by weight of the test compound dissolved in distilled water for injections and adjusted to pH 7 to 8 as required.

Specifically, a male Japanese rabbit of body weight 2.5–3.0 kg was placed in a pillory to fix its head. A single dose of 0.1 ml of the test solution was instilled into its right eye. The symptoms experienced by the anterior portion of the right eye were observed over a period of seven days and the irritation observed was scored. The results are shown in Table 2, in each case averaged over the four rabbits in each test group.

TABLE 2

| Cpd | Site | Average score at hours | | | | | days | Maximum possible score |
|---|---|---|---|---|---|---|---|---|
| | | 1 | 24 | 48 | 72 | 96 | 7 | |
| A | cornea | 0 | 0 | 0 | 0 | 0 | 0 | 80 |
| (20%) | iris | 0 | 0 | 0 | 0 | 0 | 0 | 10 |
| | conjunctiva | 0.7 | 0 | 0 | 0 | 0 | 0 | 20 |
| | average | 0.7 | 0 | 0 | 0 | 0 | 0 | 110 |
| B | cornea | 0 | 0 | 0 | 0 | 0 | 0 | — |
| (10%) | iris | 0 | 0 | 0 | 0 | 0 | 0 | — |
| | conjunctiva | 1.3 | 0 | 0 | 0 | 0 | 0 | — |
| | average | 1.3 | 0 | 0 | 0 | 0 | 0 | — |
| C | cornea | 0 | 0 | 0 | 0 | 0 | 0 | — |
| (10%) | iris | 0 | 0 | 0 | 0 | 0 | 0 | — |
| | conjunctiva | 1.3 | 0 | 0 | 0 | 0 | 0 | — |
| | average | 1.3 | 0 | 0 | 0 | 0 | 0 | — |

As can be seen from the data in the above Table, the test solutions cause little irritation, even at such high concentrations as 10 or 20% by weight, and the irritation is of such an extent that congestion of the conjunctiva is only transient. According to the evaluation method of Kay and Calandra. it is therefore considered that all of these test solutions show practically no irritation.

EXAMPLE 9

Acute Toxicity

The $LD_{50}$ value, mg/kg, on oral administration to RFVL type mice for each of Compounds A and D is shown in Table 3.

TABLE 3

| Sex | Compound | |
|---|---|---|
| | A | D |
| male | 3030 | 1800 |
| female | 3150 | 2000 |

From the above results, it can be seen that the compounds of the invention are relatively non-toxic and are valuable as ophthalmic anti-inflammatory agents.

We claim:

1. A method for the treatment or prophylaxis of ocular inflammation comprising applying to the surface of the mammalian eye an anti-inflammatory effective amount of a phenylacetic acid derivative of the formula:

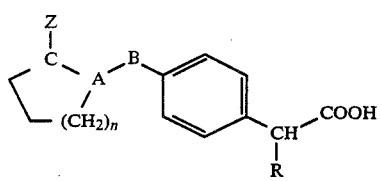

wherein:
R represents the hydrogen atom or the methyl group;
>A—B— represents a >CH—CH₂— or >C=CH— group;
>C—Z represents a >C=O (carbonyl) group or a >CH—OH group; and
n is 1 or 2;
or an ophthalmically acceptable salt or ester thereof.

2. The method of claim 1, wherein R is methyl.

3. The method of claim 1, wherein said agent is selected from the group consisting of:

2-[4-(2-oxocyclopentylmethyl)phenyl]propionic acid;
2-[4-(2-oxocyclopentylmethyl)phenyl]acetic acid;
2-[4-(2-oxocyclohexylmethyl)phenyl]propionic acid;
2-[4-(2-oxocyclopentylidenemethyl)phenyl]propionic acid;
2-[4-(2-oxocyclohexylidenemethyl)phenyl]propionic acid;
2-[4-(2-hydroxycyclopentylidenemethyl)phenyl]propionic acid;
2-[4-(2-hydroxycyclohexylidenemethyl)phenyl]propionic acid;
2-[4-(trans-2-hydroxycyclopentylmethyl)phenyl]propionic acid;
2-[4-(trans-2-hydroxycyclohexylmethyl)phenyl]propionic acid;
2-[4-(cis-2-hydroxycyclopentylmethyl)phenyl]propionic acid; and
2-[4-(cis-2-hydroxycyclohexylmethyl)phenyl]propionic acid and ophthalmically acceptable salts and esters thereof.

4. The method of claim 1, wherein said mammalian eye is a human eye.

5. The method of claim 1, wherein an eyedrop formulation is instilled into the eye.

6. The method of claim 1, wherein an eye lotion is applied to the surface of said eye.

7. The method of claim 1, wherein an eye ointment is applied to the surface of said eye.

8. A method for the treatment or prophylaxis of ocular inflammation comprising applying to the surface of the mammalian eye an anti-inflammatory effective amount of a phenylacetic acid derivative selected from the group consisting of:

sodium 2-[4-(2-oxocyclopentylmethyl)phenyl]propionate;
sodium 2-[4-(2-oxocyclohexylidenemethyl)phenyl]propionate;
sodium 2-[4-(trans-2-hydroxycyclopentylmethyl)phenyl]propionate; and
2-[4-(2-oxocyclohexylidenemethyl)phenyl]propionic acid.

9. The method of claim 8, wherein said mammalian eye is a human eye.

10. The method of claim 9, wherein an eyedrop formulation is instilled into the eye.

11. The method of claim 9, wherein an eye lotion is applied to the surface of said eye.

12. The method of claim 9, wherein an eye ointment is applied to the surface of said eye.

13. The method of claim 3, wherein an eyedrop formulation is instilled into the eye.

14. The method of claim 3, wherein an eye lotion is applied to the surface of said eye.

15. The method of claim 3, wherein an eye ointment is applied to the surface of said eye.

16. The method of claim 9, wherein said phenylacetic derivative is sodium 2-[4-(2-oxocyclopentylmethyl)phenyl]propionate.

17. The method of claim 9, wherein said phenylacetic derivative is sodium 2-[4-(2-oxocyclohexylidenemethyl)phenyl]propionate.

18. The method of claim 9, wherein said phenylacetic derivative is sodium 2-[4-(trans-2-hydroxycyclopentylmethyl)phenyl]propionate.

19. The method of claim 9, wherein said phenylacetic derivative is 2-[4-(2-oxocyclohexylidenemethyl)phenyl]propionic acid.

* * * * *